(12) United States Patent
Jackson

(10) Patent No.: US 10,363,338 B2
(45) Date of Patent: Jul. 30, 2019

(54) RESILIENT ABSORBENT COFORM NONWOVEN WEB

(71) Applicant: Kimberly-Clark Worldwide, Inc., Neenah, WI (US)

(72) Inventor: David M. Jackson, Alpharetta, GA (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 395 days.

(21) Appl. No.: 15/134,608

(22) Filed: Apr. 21, 2016

(65) Prior Publication Data

US 2016/0228596 A1 Aug. 11, 2016

Related U.S. Application Data

(63) Continuation of application No. 12/643,051, filed on Dec. 21, 2009, now abandoned.

(51) Int. Cl.
*D04H 1/56* (2006.01)
*A61F 13/15* (2006.01)
(Continued)

(52) U.S. Cl.
CPC ........ *A61L 15/24* (2013.01); *A61F 13/15658* (2013.01); *A61F 13/538* (2013.01);
(Continued)

(58) Field of Classification Search
CPC .................................................... A61L 15/24
(Continued)

(56) References Cited

U.S. PATENT DOCUMENTS 3,034,180 A 5/1962 Greiner et al.
3,110,609 A 11/1963 Bletzinger
(Continued)

FOREIGN PATENT DOCUMENTS

EP 0 333 228 A2 9/1989
EP 0 604 736 A2 7/1994
(Continued)

OTHER PUBLICATIONS

Srinivas, S. et al., "Elastic Nonwoven Fabrics from Polyolefin Elastomers," (Vistamaxx™), Society of Plastics Engineers Annual Technical Conference (ANTEC), vol. 3, May 2005, Boston, MA, pp. 1247-1251.
(Continued)

*Primary Examiner* — Mary Lynn F Theisen

(57) ABSTRACT

A resilient coform nonwoven web that contains a matrix of meltblown fibers and an absorbent material is provided. The meltblown fibers may constitute from 45 wt % to about 99 wt % of the web and the absorbent material may constitute from about 1 wt % to about 55 wt % of the web. The meltblown fibers may be formed from a thermoplastic composition that contains at least one propylene/α-olefin copolymer having a propylene content of from about 60 mole % to about 99.5 mole % and an α-olefin content of from about 0.5 mole % to about 40 mole %. The copolymer may have a density of from about 0.86 to about 0.90 grams per cubic centimeter and the thermoplastic composition may have a melt flow rate of from about 200 to about 6000 grams per 10 minutes, determined at 230° C. in accordance with ASTM Test Method D1238-E. The coform web may be imparted with a three-dimensional texture by, for example, using a three-dimensional forming surface. As one example, the resilient coform web is suitable for use as a component in the absorbent core of a personal care absorbent product.

20 Claims, 8 Drawing Sheets

(51) Int. Cl.
*A61L 15/24* (2006.01)
*D04H 1/407* (2012.01)
*D04H 1/4282* (2012.01)
*D04H 3/005* (2012.01)
*D04H 3/16* (2006.01)
*D04H 5/08* (2012.01)
*D01D 5/098* (2006.01)
*D01F 6/30* (2006.01)
*D01F 11/06* (2006.01)
*A61F 13/538* (2006.01)
*A61L 15/60* (2006.01)

(52) U.S. Cl.
CPC ............ *A61L 15/60* (2013.01); *D01D 5/0985* (2013.01); *D01F 6/30* (2013.01); *D01F 11/06* (2013.01); *D04H 1/407* (2013.01); *D04H 1/4282* (2013.01); *D04H 1/56* (2013.01); *D04H 3/005* (2013.01); *D04H 3/16* (2013.01); *D04H 5/08* (2013.01); *Y10T 442/68* (2015.04)

(58) Field of Classification Search
USPC ........................................................ 264/121
See application file for complete search history.

(56) References Cited

U.S. PATENT DOCUMENTS

| | | | |
|---|---|---|---|
| 4,042,740 A | 8/1977 | Krueger | |
| 4,100,324 A | 7/1978 | Anderson et al. | |
| 4,103,058 A | 7/1978 | Humlicek | |
| 4,531,945 A | 7/1985 | Allison | |
| 4,637,819 A | 1/1987 | Ouellette et al. | |
| 4,724,114 A | 2/1988 | McFarland et al. | |
| 4,741,941 A | 5/1988 | Englebert et al. | |
| 4,762,521 A | 8/1988 | Roessler et al. | |
| 4,879,170 A | 11/1989 | Radwanski et al. | |
| 5,096,995 A | 3/1992 | Fukumoto et al. | |
| 5,149,335 A | 9/1992 | Kellenberger et al. | |
| 5,180,620 A | 1/1993 | Mende | |
| 5,213,881 A | 5/1993 | Timmons et al. | |
| 5,242,632 A | 9/1993 | Mende | |
| 5,350,624 A | 9/1994 | Georger et al. | |
| 5,423,786 A | 6/1995 | Fung et al. | |
| 5,508,102 A | 4/1996 | Georger et al. | |
| 5,562,645 A | 10/1996 | Tanzer et al. | |
| 5,575,874 A | 11/1996 | Griesbach, III et al. | |
| 5,604,284 A | 2/1997 | Ueda et al. | |
| 5,643,653 A | 7/1997 | Griesbach, III et al. | |
| 5,652,326 A | 7/1997 | Ueda et al. | |
| 5,665,396 A | 9/1997 | Ulman | |
| 5,672,248 A | 9/1997 | Wendt et al. | |
| 5,733,274 A | 3/1998 | Osborn, III | |
| 5,858,292 A | 1/1999 | Dragoo et al. | |
| 5,886,098 A | 3/1999 | Ueda et al. | |
| 5,952,251 A * | 9/1999 | Jackson | D04H 1/54 442/340 |
| 5,964,743 A | 10/1999 | Abuto et al. | |
| 5,969,026 A | 10/1999 | Mor et al. | |
| 6,010,588 A | 1/2000 | Stahl et al. | |
| 6,039,839 A | 3/2000 | Trokhan et al. | |
| 6,127,595 A | 10/2000 | Makoui et al. | |
| 6,231,557 B1 | 5/2001 | Krautkramer et al. | |
| 6,245,051 B1 | 6/2001 | Zenker et al. | |
| 6,362,389 B1 | 3/2002 | McDowall et al. | |
| 6,468,626 B1 | 10/2002 | Takai et al. | |
| 6,627,789 B1 | 9/2003 | Vandenbogart et al. | |
| 6,680,423 B1 | 1/2004 | Tanzer | |
| 6,810,553 B1 | 11/2004 | Otsuji et al. | |
| 6,844,481 B2 | 1/2005 | Taneichi et al. | |
| 6,896,669 B2 | 5/2005 | Krautkramer et al. | |
| 7,101,622 B2 | 9/2006 | Chang et al. | |
| 7,594,904 B2 | 9/2009 | Rosenfeld et al. | |
| 7,662,745 B2 | 2/2010 | Zhang et al. | |
| 8,043,984 B2 | 10/2011 | Stadelman et al. | |
| 2002/0155776 A1 | 10/2002 | Mitchler et al. | |
| 2003/0077970 A1 | 4/2003 | Delucia et al. | |
| 2003/0113463 A1 | 6/2003 | Ko et al. | |
| 2003/0120233 A1 | 6/2003 | Ohshima et al. | |
| 2003/0120249 A1 | 6/2003 | Wulz et al. | |
| 2003/0135178 A1 | 7/2003 | Hansen | |
| 2003/0149411 A1 | 8/2003 | Keuhn et al. | |
| 2003/0176136 A1 | 9/2003 | Wadsworth | |
| 2003/0200991 A1 | 10/2003 | Keck et al. | |
| 2003/0211802 A1 | 11/2003 | Keck et al. | |
| 2003/0236511 A1 | 12/2003 | Jones et al. | |
| 2004/0005457 A1 | 1/2004 | Delucia et al. | |
| 2004/0054343 A1 | 3/2004 | Barnett et al. | |
| 2004/0102751 A1 | 5/2004 | Schueler | |
| 2004/0253892 A1 | 12/2004 | Baker et al. | |
| 2004/0265534 A1 | 12/2004 | Curro et al. | |
| 2005/0061356 A1 | 3/2005 | Wong et al. | |
| 2005/0148261 A1 | 7/2005 | Close et al. | |
| 2005/0228350 A1 | 10/2005 | Ranganathan et al. | |
| 2006/0004336 A1 | 1/2006 | Zhang et al. | |
| 2006/0052022 A1 | 3/2006 | Suzuki et al. | |
| 2006/0058761 A1 | 3/2006 | Kudo et al. | |
| 2006/0063456 A1 | 3/2006 | Carter | |
| 2006/0141881 A1 | 6/2006 | Bergsten et al. | |
| 2006/0184149 A1 | 8/2006 | Kasai et al. | |
| 2006/0199006 A1 | 9/2006 | Poon et al. | |
| 2007/0049153 A1 | 3/2007 | Dunbar et al. | |
| 2007/0065643 A1 | 3/2007 | Kopacz et al. | |
| 2007/0135785 A1 | 6/2007 | Qin et al. | |
| 2007/0197117 A1 | 8/2007 | Austin et al. | |
| 2008/0119103 A1 | 5/2008 | Ng et al. | |
| 2008/0177242 A1 | 7/2008 | Chang et al. | |
| 2008/0199673 A1* | 8/2008 | Allgeuer | D04H 1/4291 428/219 |
| 2009/0062760 A1 | 3/2009 | Wright et al. | |
| 2009/0111347 A1 | 4/2009 | Peng et al. | |
| 2009/0233049 A1* | 9/2009 | Jackson | A47L 13/16 428/156 |
| 2010/0029162 A1* | 2/2010 | Datta | C08L 23/10 442/400 |
| 2011/0152808 A1 | 6/2011 | Jackson | |

FOREIGN PATENT DOCUMENTS

| | | |
|---|---|---|
| EP | 0 617 940 A2 | 10/1994 |
| EP | 1 241 288 A2 | 9/2002 |
| EP | 0 794 751 B2 | 1/2003 |
| EP | 1 634 556 A1 | 3/2006 |
| JP | 11-286863 A | 10/1999 |
| JP | 2005-145020 A | 6/2005 |
| JP | 2006-002303 A | 1/2006 |
| JP | 2008-025079 A | 2/2008 |
| KR | 10-2006-0129240 A | 12/2006 |
| KR | 10-2006-0130230 A | 12/2006 |
| KR | 10-2009-0014302 A | 2/2009 |
| KR | 10-2009-0117829 A | 11/2009 |
| WO | WO 1998/003133 A2 | 1/1998 |
| WO | WO 2004/062528 A2 | 7/2004 |
| WO | WO 2005/111282 A1 | 11/2005 |
| WO | WO 2007/024447 A1 | 3/2007 |
| WO | WO 2008/073101 A1 | 6/2008 |
| WO | WO 2009/032869 A1 | 3/2009 |

OTHER PUBLICATIONS

VISTAMAXX™ 2320 MDC Datasheet, ExxonMobil Chemical, printed from Internet page www.materialdatacenter.com Feb. 4, 2015.

* cited by examiner

RESILIENT ABSORBENT COFORM NONWOVEN WEB

BACKGROUND OF THE INVENTION

Coform nonwoven webs, which are composites of a matrix of meltblown fibers and an absorbent material (e.g., pulp fibers), have been used as an absorbent layer in a wide variety of applications, including absorbent articles, absorbent dry wipes, wet wipes, and mops. Most conventional coform webs employ meltblown fibers formed from polypropylene homopolymers. One problem sometimes experienced with such coform materials, however, is that coform materials may not be sufficiently resilient when subjected to bending forces. For example, when a coform wiper is crumpled, perhaps to wring a fluid from the wiper, the coform material may not return to its original flat, unwrinkled state. As another example, a coform material used as an absorbent core in personal care absorbent product may have a tendency for bunching.

As such, a need currently exists for an improved coform nonwoven web for use in a variety of applications that shows improved resistance to bending forces and demonstrates a tendency to return to a flat state after being folded.

SUMMARY OF THE INVENTION

In accordance with one embodiment of the present invention, a resilient coform nonwoven web is disclosed that includes a matrix of meltblown fibers and an absorbent material. The meltblown fibers constitute from 45 wt % to about 99 wt % of the web and the absorbent material constitutes from about 1 wt % to about 55 wt % of the web. The meltblown fibers are formed from a thermoplastic composition that contains at least one propylene/α-olefin copolymer having a propylene content of from about 60 mole % to about 99.5 mole % and an α-olefin content of from about 0.5 mole % to about 40 mole %. The copolymer further has a density of from about 0.86 to about 0.90 grams per cubic centimeter and the thermoplastic composition has melt flow rate of from about 200 to about 6000 grams per 10 minutes, determined at 230° C. in accordance with ASTM Test Method D1238-E. In another embodiment, the α-olefin includes ethylene. In a further embodiment, the propylene constitutes from about 85 mole % to about 98 mole % of the copolymer and the α-olefin constitutes from about 2 mole % to about 15 mole % of the copolymer. In an even further embodiment, the copolymer has a density of from about 0.861 to about 0.89 grams per cubic centimeter, and preferably from about 0.862 to about 0.88 grams per cubic centimeter. In another embodiment, the propylene copolymer is single-site catalyzed. In a further embodiment, the propylene/α-olefin copolymer constitutes from about 15 wt % to about 99.9 wt % of the thermoplastic composition.

In one embodiment, the melt flow rate of the thermoplastic composition is from about 170 to about 1500 grams per 10 minutes.

In one embodiment, the thermoplastic composition includes from about 0.001 wt % to about 15 wt % of a surfactant.

In one embodiment, the absorbent material includes pulp fibers. In a further embodiment, the absorbent material comprises superabsorbent polymer particles or superabsorbent polymer fibers.

In one embodiment, the meltblown fibers constitute from 50 wt % to about 90 wt % of the web and the absorbent material constitutes from about 10 wt % to about 50 wt % of the web.

In one embodiment, the web defines an exterior surface having a three-dimensional texture that includes a plurality of peaks and valleys.

In one embodiment, an absorbent personal care article includes the resilient coform nonwoven web described above. In a further embodiment, an absorbent personal care article includes a body-side liner, an absorbent core including the resilient coform nonwoven web described above, and a garment-side baffle.

In accordance with another embodiment of the present invention, a method of forming a resilient coform nonwoven web is disclosed that includes merging together a stream of an absorbent material with a stream of meltblown fibers to form a composite stream. The meltblown fibers constitute from 45 wt % to about 99 wt % of the web and the absorbent material constitutes from about 1 wt % to about 55 wt % of the web. The meltblown fibers are formed from a thermoplastic composition that contains at least one propylene/α-olefin copolymer having a propylene content of from about 60 mole % to about 99.5 mole % and an α-olefin content of from about 0.5 mole % to about 40 mole %, wherein the copolymer further has a density of from about 0.86 to about 0.90 grams per cubic centimeter and the composition has a melt flow rate of from about 120 to about 6000 grams per 10 minutes, determined at 230° C. in accordance with ASTM Test Method D1238-E. Thereafter, the composite stream is collected on a forming surface to form a resilient coform nonwoven web.

In one embodiment, the melt flow rate of the thermoplastic composition is from about 170 to about 1500 grams per 10 minutes.

In one embodiment, the thermoplastic composition comprises from about 0.001 wt % to about 15 wt % of a surfactant.

In one embodiment, the stream of absorbent material is merged together with first and second streams of meltblown fibers. In a further embodiment, the first stream and second stream of meltblown fibers are supplied from respective first and second die heads, each of which is oriented at an angle of from about 45° to 55° relative to a plane tangent to the die heads.

In one embodiment, the web is collected on a textured surface to define an exterior web surface having a three-dimensional texture that includes a plurality of peaks and valleys.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
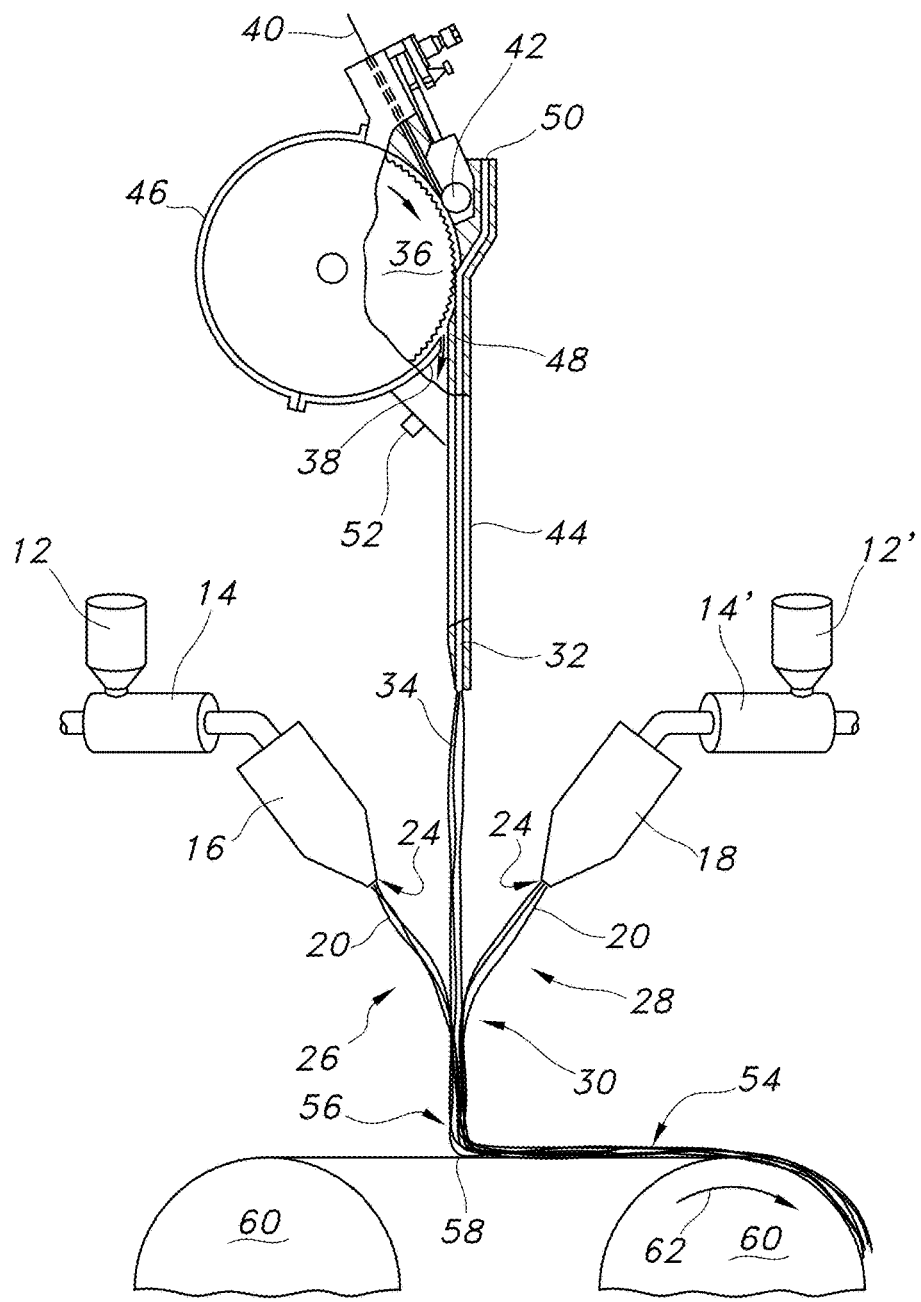
FIG. 1 is a schematic illustration one embodiment of a method for forming the coform web of the present invention.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

As used herein the term "nonwoven web" generally refers to a web having a structure of individual fibers or threads which are interlaid, but not in an identifiable manner as in a knitted fabric. Examples of nonwoven fabrics or webs include, but are not limited to, meltblown webs, spunbond webs, bonded carded webs, airlaid webs, coform webs, hydraulically entangled webs, and so forth.

As used herein, the term "meltblown web" generally refers to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 micrometers in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 micrometers, and are often between about 5 to about 20 micrometers.

Generally speaking, the present invention is directed to a coform nonwoven web that contains a matrix of meltblown fibers and an absorbent material. The meltblown fibers constitute from 45 wt % to about 99 wt % of the web and the absorbent material constitutes from about 1 wt % to about 55 wt % of the web. The meltblown fibers are formed from a thermoplastic composition that contains at least one propylene/α-olefin copolymer of a certain monomer content, density, melt flow rate, etc. The selection of a specific type of propylene/α-olefin copolymer provides the resulting composition with improved thermal properties for forming a coform web. For example, the thermoplastic composition crystallizes at a relatively slow rate, thereby allowing the fibers to remain slightly tacky during formation. This tackiness may provide a variety of benefits, such as enhancing the ability of the meltblown fibers to adhere to the absorbent material during web formation. The meltblown fibers may constitute from about 45 wt % to about 99 wt %, in particular embodiments from about 50 wt % to about 90 wt %, and in more particular embodiments, from about 50 wt % to about 80 wt % of the coform web. Likewise, the absorbent material may constitute from about 1 wt % to about 55 wt %, in particular embodiments from 10 wt % to about 50 wt %, and in more particular embodiments, from about 20 wt % to about 50 wt % of the coform web.

In addition to enhancing the bonding capacity of the meltblown fibers, the thermoplastic composition of the present invention may also impart other benefits to the resulting coform structure. In certain embodiments, for example, the coform web may be imparted with texture using a three-dimensional forming surface. In such embodiments, the relatively slow rate of crystallization of the meltblown fibers may increase their ability to conform to the contours of the three-dimensional forming surface. Once the fibers crystallize, however, the meltblown fibers may achieve a degree of resiliency greater than that of conventional polypropylene, thereby allowing them to both retain and regain the three-dimensional shape and highly textured surface on the coform web.

Another benefit of the fiber's prolonged tackiness during formation may be an increased ply attachment strength between layers of a multi-ply coform nonwoven web, resulting in additional shear energy being necessary to delaminate the plies. Such increased ply attachment strength may reduce or eliminate the need for embossing that could negatively impact sheet characteristics such as thickness and density. Increased ply attachment strength may be particularly desirable during dispensing of wipers made from a multi-ply coform nonwoven web. Texture imparted by using a three-dimensional forming surface as described herein may further increase the ply attachment strength by increasing the contact surface area between the plies.

Various embodiments of the present invention will now be described in more detail.

I. Thermoplastic Composition

The thermoplastic composition of the present invention contains at least one copolymer of propylene and an α-olefin, such as a $C_2$-$C_{20}$ α-olefin, $C_2$-$C_{12}$ α-olefin, or $C_2$-$C_8$ α-olefin. Suitable α-olefins may be linear or branched (e.g., one or more $C_1$-$C_3$ alkyl branches, or an aryl group). Specific examples include ethylene, butene; 3-methyl-1-butene; 3,3-dimethyl-1-butene; pentene; pentene with one or more methyl, ethyl or propyl substituents; hexane with one or more methyl, ethyl or propyl substituents; heptene with one or more methyl, ethyl or propyl substituents; octene with one or more methyl, ethyl or propyl substituents; nonene with one or more methyl, ethyl or propyl substituents; ethyl, methyl or dimethyl-substituted decene; dodecene; styrene; and so forth. Particularly desired α-olefin comonomers are ethylene, butene (e.g., 1-butene), 7exane, and octene (e.g., 1-octene or 2-octene). The propylene content of such copolymers may be from about 60 mole % to about 99.5 mole %, in further embodiments from about 80 mole % to about 99 mole %, and in even further embodiments, from about 85 mole % to about 98 mole %. The α-olefin content may likewise range from about 0.5 mole % to about 40 mole %, in further embodiments from about 1 mole % to about 20 mole %, and in even further embodiments, from about 2 mole % to about 15 mole %. The distribution of the α-olefin comonomer is typically random and uniform among the differing molecular weight fractions forming the propylene copolymer.

The density of the propylene/α-olefin copolymer may be a function of both the length and amount of the α-olefin. That is, the greater the length of the α-olefin and the greater the amount of α-olefin present, the lower the density of the copolymer. Generally speaking, copolymers with a higher density are better able to form a three-dimensional structure, while those with a lower density possess better elastomeric and resiliency properties. Thus, to achieve an optimum balance between texture and resiliency, the propylene/α-olefin copolymer is normally selected to have a density of about 0.860 grams per cubic centimeter (g/cm$^3$) to about 0.900 g/cm$^3$, in further embodiments from about 0.861 to about 0.890 g/cm$^3$, and in even further embodiments, from about 0.862 g/cm$^3$ to about 0.880 g/cm$^3$. Further, the density of the thermoplastic composition is normally selected to have a density of about 0.860 grams per cubic centimeter (g/cm$^3$) to about 0.940 g/cm$^3$, in further embodiments from about 0.861 to about 0.920 g/cm$^3$, and in even further embodiments, from about 0.862 g/cm$^3$ to about 0.900 g/cm$^3$.

Any of a variety of known techniques may generally be employed to form the propylene/α-olefin copolymer used in the meltblown fibers. For instance, olefin polymers may be formed using a free radical or a coordination catalyst (e.g., Ziegler-Natta). Preferably, the copolymer is formed from a single-site coordination catalyst, such as a metallocene catalyst. Such a catalyst system produces propylene copolymers in which the co-monomer is randomly distributed within a molecular chain and uniformly distributed across the different molecular weight fractions. Metallocene-catalyzed propylene copolymers are described, for instance, in U.S. Pat. No. 7,105,609 to Datta, et al.; U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled tacticity.

In particular embodiments the propylene/α-olefin copolymer constitutes about 50 wt % or more, in further embodiments about from 60 wt % or more, and in even further embodiments, about 75 wt % or more of the thermoplastic composition used to form the meltblown fibers. In other embodiments the propylene/α-olefin copolymer constitutes at least about 1 wt % and less than about 49 wt %, in particular embodiments from at least about 1% and less than about 45 wt %, in further embodiments from at least about 5% and less than about 45 wt %, and in even further embodiments, from at least about 5 wt % and less than about 35 wt % of the thermoplastic composition used to form the meltblown fibers. Of course, other thermoplastic polymers may also be used to form the meltblown fibers so long as they do not adversely affect the desired properties of the composite. For example, the meltblown fibers may contain other polyolefins (e.g., polypropylene, polyethylene, etc.), polyesters, polyurethanes, polyamides, block copolymers, and so forth. In one embodiment, the meltblown fibers may contain an additional propylene polymer, such as homo polypropylene or a copolymer of propylene. The additional propylene polymer may, for instance, be formed from a substantially isotactic polypropylene homopolymer or a copolymer containing equal to or less than about 10 weight percent of other monomer, i.e., at least about 90% by weight propylene. Such a polypropylene may be present in the form of a graft, random, or block copolymer and may be predominantly crystalline in that it has a sharp melting point above about 110° C., in further embodiments about above 115° C., and in even further embodiments, above about 130° C. Examples of such additional polypropylenes are described in U.S. Pat. No. 6,992,159 to Datta, et al., which is incorporated herein in its entirety by reference thereto for all purposes.

In particular embodiments, additional polymer(s) may constitute from about 0.1 wt % to about 90 wt %, in further embodiments from about 0.5 wt % to about 50 wt %, and in even further embodiments, from about 1 wt % to about 30 wt % of the thermoplastic composition. Likewise, the above-described propylene/α-olefin copolymer may constitute from about 15 wt % to about 99.9 wt %, in further embodiments from about 50 wt % to about 99.5 wt %, and in even further embodiments, from about 70 wt % to about 99 wt % of the thermoplastic composition.

The thermoplastic composition used to form the meltblown fibers may also contain other additives as is known in the art, such as surfactants, melt stabilizers, processing stabilizers, heat stabilizers, light stabilizers, antioxidants, heat aging stabilizers, whitening agents, etc. Phosphite stabilizers (e.g., IRGAFOS available from Ciba Specialty Chemicals of Tarrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant. Some suitable hindered phenols include those available from Ciba Specialty Chemicals (Ciba) of under the trade name "Irganox®", such as Irganox® 1076, 1010, or E 201. When employed, such additives (e.g., antioxidant, stabilizer, surfactants, etc.) may each be present in an amount from about 0.001 wt % to about 15 wt %, in further embodiments, from about 0.005 wt % to about 10 wt %, and in even further embodiments, from about 0.01 wt % to about 5 wt % of the thermoplastic composition used to form the meltblown fibers. One or more surfactants may be added to the polymer composition to make the polymer fibers more wettable and improve the fluid intake properties of the coform material. Suitable surfactants include cationic, anionic, amphoteric, and nonionic surfactants. A particularly suitable internal surfactant is available from Ciba is IRGASURF HL 560. When employed, the surfactant may each be present in an amount from about 0.5 wt % to about 10 wt %, in further embodiments, from about 1.0 wt % to about 7.5 wt %, and in even further embodiments, from about 1.5 wt % to about 5 wt % of the thermoplastic composition used to form the meltblown fibers. Surfactants may also be applied to the meltblown fibers externally as topical treatments.

Through the selection of certain polymers and their content, the resulting thermoplastic composition may possess thermal properties superior to polypropylene homopolymers conventionally employed in meltblown webs. For example, the thermoplastic composition is generally more amorphous in nature than polypropylene homopolymers conventionally employed in meltblown webs. For this reason, the rate of crystallization of the thermoplastic composition is slower, as measured by its "crystallization half-time"—i.e., the time required for one-half of the material to become crystalline. For example, the thermoplastic composition typically has a crystallization half-time of greater than about 5 minutes, in further embodiments from about 5.25 minutes to about 20 minutes, and in even further embodiments, from about 5.5 minutes to about 12 minutes, determined at a temperature of 125° C. To the contrary, conventional polypropylene homopolymers often have a crystallization half-time of 5 minutes or less. Further, the thermoplastic composition may have a melting temperature ("$T_m$") of from about 100° C. to about 250° C., in further embodiments from about 110° C. to about 200° C., and in even further embodiments, from about 140° C. to about 180° C. The thermoplastic composition may also have a crystallization temperature ("$T_c$") (determined at a cooling rate of 10° C./min) of from about 50° C. to about 150° C., in further embodiments from about 80° C. to about 140° C., and in even further embodiments, from about 100° C. to about 120° C. The crystallization half-time, melting temperature, and crystallization temperature may be determined using differential scanning calorimetry ("DSC") as is well known to those skilled in the art.

The melt flow rate of the thermoplastic composition may also be selected within a certain range to optimize the properties of the resulting meltblown fibers. The melt flow rate is the weight of a polymer (in grams) that may be forced through an extrusion rheometer orifice (0.0825-inch diameter) when subjected to a force of 2160 grams in 10 minutes at 230° C. Generally speaking, the melt flow rate is high enough to improve melt processability, but not so high as to adversely interfere with the binding properties of the fibers to the absorbent material. Thus, in most embodiments of the present invention, the thermoplastic composition has a melt flow rate of from about 120 to about 6000 grams per 10 minutes, in further embodiments from about 150 to about 3000 grams per 10 minutes, and in even further embodiments, from about 170 to about 1500 grams per 10 minutes, measured in accordance with ASTM Test Method D1238-E.

II. Meltblown Fibers

The meltblown fibers may be monocomponent or multicomponent. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference thereto for all purposes.

III. Absorbent Material

Any absorbent material may generally be employed in the coform nonwoven web, such as absorbent fibers, particles, etc. In one embodiment, the absorbent material includes fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Weyerhaeuser Co. of Federal Way, Wash. under the designation "Weyco CF-405." Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, and so forth. In addition, in some instances, synthetic fibers can also be utilized.

Besides or in conjunction with pulp fibers, the absorbent material may also include a superabsorbent that is in the form fibers, particles, gels, etc. Generally speaking, superabsorbents are water-swellable materials capable of absorbing at least about 20 times its weight and, in some cases, at least about 30 times its weight in an aqueous solution containing 0.9 weight percent sodium chloride. The superabsorbent may be formed from natural, synthetic and modified natural polymers and materials. Examples of synthetic superabsorbent polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further, superabsorbents include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Particularly suitable superabsorbent polymers are HYSORB 8800AD (BASF of Charlotte, N.C. and FAVOR SXM 9300 (available from Evonik Stockhausen of Greensboro, N.C.).

IV. Coform Technique

The coform web of the present invention is generally made by a process in which at least one meltblown die head (e.g., two) is arranged near a chute through which the absorbent material is added while the web forms. Some examples of such coform techniques are disclosed in U.S. Pat. No. 4,100,324 to Anderson, et al.; U.S. Pat. No. 5,350,624 to Georger, et al.; and U.S. Pat. No. 5,508,102 to Georger, et al., as well as U.S. Patent Application Publication Nos. 2003/0200991 to Keck, et al. and 2007/0049153 to Dunbar, et al., all of which are incorporated herein in their entirety by reference thereto for all purposes.

Referring to FIG. 1, for example, one embodiment of an apparatus is shown for forming a coform web of the present invention. In this embodiment, the apparatus includes a pellet hopper 12 or 12' of an extruder 14 or 14', respectively, into which a propylene/α-olefin thermoplastic composition may be introduced. The extruders 14 and 14' each have an extrusion screw (not shown), which is driven by a conventional drive motor (not shown). As the polymer advances through the extruders 14 and 14', it is progressively heated to a molten state due to rotation of the extrusion screw by the drive motor. Heating may be accomplished in a plurality of discrete steps with its temperature being gradually elevated as it advances through discrete heating zones of the extruders 14 and 14' toward two meltblowing dies 16 and 18, respectively. The meltblowing dies 16 and 18 may be yet another heating zone where the temperature of the thermoplastic resin is maintained at an elevated level for extrusion.

When two or more meltblowing die heads are used, such as described above, it should be understood that the fibers produced from the individual die heads may be different types of fibers. That is, one or more of the size, shape, or polymeric composition may differ, and furthermore the fibers may be monocomponent or multicomponent fibers. For example, larger fibers may be produced by the first meltblowing die head, such as those having an average diameter of about 10 micrometers or more, in further embodiments about 15 micrometers or more, and in even further embodiments, from about 20 to about 50 micrometers, while smaller fibers may be produced by the second die head, such as those having an average diameter of about 10 micrometers or less, in further embodiments about 7 micrometers or less, and in even further embodiments, from about 2 to about 6 micrometers. In addition, it may be desirable that each die head extrude approximately the same amount of polymer such that the relative percentage of the basis weight of the coform nonwoven web material resulting from each meltblowing die head is substantially the same. Alternatively, it may also be desirable to have the relative basis weight production skewed, such that one die head or the other is responsible for the majority of the coform web in terms of basis weight. As a specific example, for a meltblown fibrous nonwoven web material having a basis weight of 1.0 ounces per square yard or "osy" (34 grams per square meter or "gsm"), it may be desirable for the first meltblowing die head to produce about 30 percent of the basis weight of the meltblown fibrous nonwoven web material, while one or more subsequent meltblowing die heads produce the remainder 70 percent of the basis weight of the meltblown fibrous nonwoven web material. Generally speaking, the overall basis weight of the coform nonwoven web is from about 10 gsm to about 350 gsm, and more particularly from about 17 gsm to about 200 gsm, and still more particularly from about 25 gsm to about 150 gsm.

Figure 2:
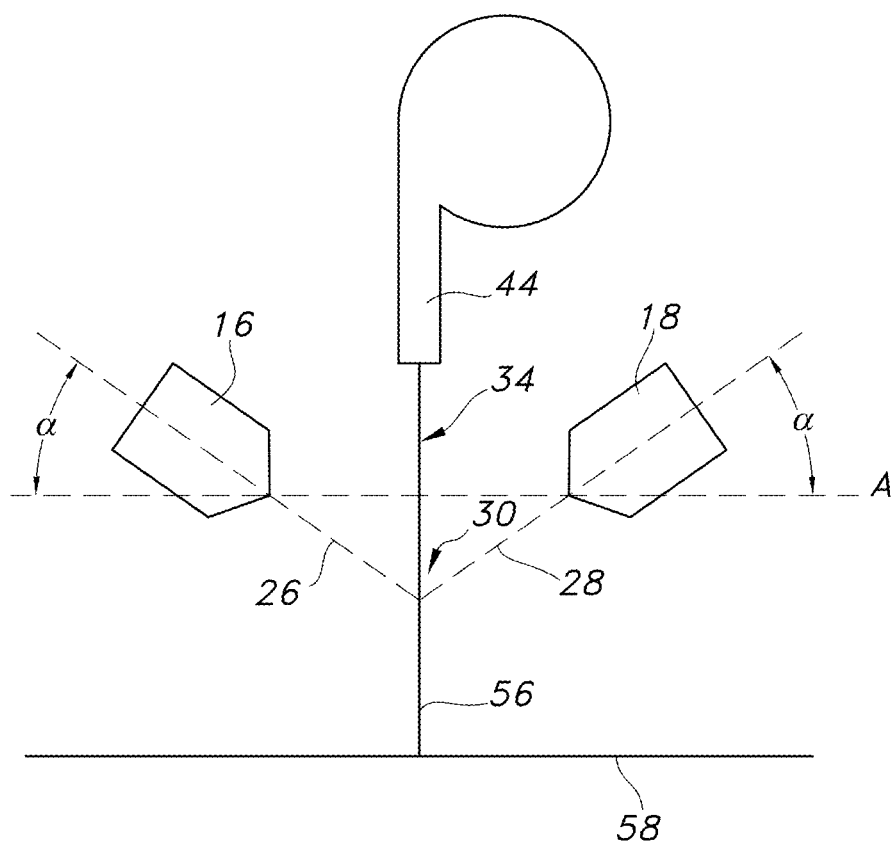
FIG. 2 is an illustration of certain features of the apparatus shown in FIG. 1.

Each meltblowing die 16 and 18 is configured so that two streams of attenuating gas per die converge to form a single stream of gas which entrains and attenuates molten threads 20 as they exit small holes or orifices 24 in each meltblowing die. The molten threads 20 are formed into fibers or, depending upon the degree of attenuation, microfibers, of a small diameter which is usually less than the diameter of the orifices 24. Thus, each meltblowing die 16 and 18 has a corresponding single stream of gas 26 and 28 containing entrained thermoplastic polymer fibers. The gas streams 26 and 28 containing polymer fibers are aligned to converge at an impingement zone 30. Typically, the meltblowing die heads 16 and 18 are arranged at a certain angle with respect to the forming surface, such as described in U.S. Pat. Nos. 5,508,102 and 5,350,624 to Georger et al. Referring to FIG. 2, for example, the meltblown dies 16 and 18 may be oriented at an angle α as measured from a plane "A" tangent to the two dies 16 and 18. As shown, the plane "A" is generally parallel to the forming surface 58 (FIG. 1). Typically, each die 16 and 18 is set at an angle ranging from about 30 to about 75 degrees, in further embodiments from about 35° to about 60°, and in even further embodiments from about 45° to about 55°. The dies 16 and 18 may be oriented at the same or different angles. In fact, the texture of the coform web may actually be enhanced by orienting one die at an angle different than another die.

Referring again to FIG. 1, absorbent fibers 32 (e.g., pulp fibers) are added to the two streams 26 and 28 of thermoplastic polymer fibers 20 and 21, respectively, and at the impingement zone 30. Introduction of the absorbent fibers 32 into the two streams 26 and 28 of thermoplastic polymer fibers 20 and 21, respectively, is designed to produce a graduated distribution of absorbent fibers 32 within the combined streams 26 and 28 of thermoplastic polymer fibers. This may be accomplished by merging a secondary gas stream 34 containing the absorbent fibers 32 between the two streams 26 and 28 of thermoplastic polymer fibers 20 and 21 so that all three gas streams converge in a controlled manner. Because they remain relatively tacky and semi-molten after formation, the meltblown fibers 20 and 21 may simultaneously adhere and entangle with the absorbent fibers 32 upon contact therewith to form a coherent nonwoven structure.

To accomplish the merger of the fibers, any conventional equipment may be employed, such as a picker roll 36 arrangement having a plurality of teeth 38 adapted to separate a mat or batt 40 of absorbent fibers into the individual absorbent fibers. When employed, the sheets or mats 40 of fibers 32 are fed to the picker roll 36 by a roller arrangement 42. After the teeth 38 of the picker roll 36 have separated the mat of fibers into separate absorbent fibers 32, the individual fibers are conveyed toward the stream of thermoplastic polymer fibers through a nozzle 44. A housing 46 encloses the picker roll 36 and provides a passageway or gap 48 between the housing 46 and the surface of the teeth 38 of the picker roll 36. A gas, for example, air, is supplied to the passageway or gap 48 between the surface of the picker roll 36 and the housing 46 by way of a gas duct 50. The gas duct 50 may enter the passageway or gap 48 at the junction 52 of the nozzle 44 and the gap 48. The gas is supplied in sufficient quantity to serve as a medium for conveying the absorbent fibers 32 through the nozzle 44.

The gas supplied from the duct 50 also serves as an aid in removing the absorbent fibers 32 from the teeth 38 of the picker roll 36. The gas may be supplied by any conventional arrangement such as, for example, an air blower (not shown). It is contemplated that additives and/or other materials may be added to or entrained in the gas stream to treat the absorbent fibers. The individual absorbent fibers 32 are typically conveyed through the nozzle 44 at about the velocity at which the absorbent fibers 32 leave the teeth 38 of the picker roll 36. In other words, the absorbent fibers 32, upon leaving the teeth 38 of the picker roll 36 and entering the nozzle 44, generally maintain their velocity in both magnitude and direction from the point where they left the teeth 38 of the picker roll 36. Such an arrangement, which is discussed in more detail in U.S. Pat. No. 4,100,324 to Anderson, et al.

If desired, the velocity of the secondary gas stream 34 may be adjusted to achieve coform structures of different properties. For example, when the velocity of the secondary gas stream is adjusted so that it is greater than the velocity of each stream 26 and 28 of thermoplastic polymer fibers 20 and 21 upon contact at the impingement zone 30, the absorbent fibers 32 are incorporated in the coform nonwoven web in a gradient structure. That is, the absorbent fibers 32 have a higher concentration between the outer surfaces of the coform nonwoven web than at the outer surfaces. On the other hand, when the velocity of the secondary gas stream 34 is less than the velocity of each stream 26 and 28 of thermoplastic polymer fibers 20 and 21 upon contact at the impingement zone 30, the absorbent fibers 32 are incorporated in the coform nonwoven web in a substantially homogenous fashion. That is, the concentration of the absorbent fibers is substantially the same throughout the coform nonwoven web. This is because the low-speed stream of absorbent fibers is drawn into a high-speed stream of thermoplastic polymer fibers to enhance turbulent mixing which results in a consistent distribution of the absorbent fibers.

To convert the composite stream 56 of thermoplastic polymer fibers 20, 21 and absorbent fibers 32 into a coform nonwoven structure 54, a collecting device is located in the path of the composite stream 56. The collecting device may be a forming surface 58 (e.g., belt, drum, wire, fabric, etc.) driven by rollers 60 and that is rotating as indicated by the arrow 62 in FIG. 1. The merged streams of thermoplastic polymer fibers and absorbent fibers are collected as a coherent matrix of fibers on the surface of the forming surface 58 to form the coform nonwoven web 54. If desired, a vacuum box (not shown) may be employed to assist in drawing the near molten meltblown fibers onto the forming surface 58. The resulting textured coform structure 54 is coherent and may be removed from the forming surface 58 as a self-supporting nonwoven material.

It should be understood that the present invention is by no means limited to the above-described embodiments. In an alternative embodiment, for example, first and second meltblowing die heads may be employed that extend substantially across a forming surface in a direction that is substantially transverse to the direction of movement of the forming surface. The die heads may likewise be arranged in a substantially vertical disposition, i.e., perpendicular to the forming surface, so that the thus-produced meltblown fibers are blown directly down onto the forming surface. Such a configuration is well known in the art and described in more detail in, for instance, U.S. Patent Application Publication No. 2007/0049153 to Dunbar, et al. Furthermore, although the above-described embodiments employ multiple meltblowing die heads to produce fibers of differing sizes, a single die head may also be employed. An example of such a process is described, for instance, in U.S. Patent Application Publication No. 2005/0136781 to Lassid, et al., which is incorporated herein in its entirety by reference thereto for all purposes.

As indicated above, it is desired in certain cases to form a coform web that is textured. Referring again to FIG. 1, for example, one embodiment of the present invention employs a forming surface 58 that is foraminous in nature so that the fibers may be drawn through the openings of the surface and form dimensional cloth-like tufts projecting from the surfaces of the material that correspond to the openings in the forming surface 58. The foraminous surface may be provided by any material that provides sufficient openings for penetration by some of the fibers, such as a highly permeable forming wire. Wire weave geometry and processing conditions may be used to alter the texture or tufts of the material. The particular choice will depend on the desired peak size, shape, depth, surface tuft "density" (that is, the number of peaks or tufts per unit area), etc. In one embodiment, for example, the wire may have an open area of from about 35% and about 65%, in further embodiments from about 40% to about 60%, and in even further embodiments, from about 45% to about 55%. One exemplary high open area forming surface is the forming wire FORMTECH™ 6 manufactured by Albany International Co. of Albany, N.Y. Such a wire has a "mesh count" of about six strands by six strands per square inch (about 2.4 by 2.4 strands per square centimeter), i.e., resulting in about 36 foramina or "holes" per square inch (about 5.6 per square centimeter), and therefore capable of forming about 36 tufts or peaks in the material per square inch (about 5.6 peaks per square centimeter). The FORMTECH™ 6 wire also has a warp diameter of about 1 millimeter polyester, a shute diameter of about 1.07 millimeters polyester, a nominal air permeability of approximately 41.8 m$^3$/min (1475 ft$^3$/min), a nominal caliper of about 0.2 centimeters (0.08 inch) and an open area of approximately 51%. Another exemplary forming surface available from the Albany International Co. is the forming wire FORMTECH™ 10, which has a mesh count of about 10 strands by 10 strands per square inch (about 4 by 4 strands per square centimeter), i.e., resulting in about 100 foramina or "holes" per square inch (about 15.5 per square centimeter), and therefore capable of forming about 100 tufts or peaks per square inch (about 15.5 peaks per square centimeter) in the material. Still another suitable forming wire is FORMTECH™ 8, which has an open area of 47% and is also available from Albany International. Of course, other forming wires and surfaces (e.g., drums, plates, mats, etc.) may be employed. For examples, mats may be used with a depressions engraved in the surface such that the coform fibers will fill the depressions to result in tufts that correspond with the depressions. The depressions (tufts) may take on various shapes, including, but not limited to, circles, squares, rectangles, swirls, ribs, lines, clouds, and so forth. Also, surface variations may include, but are not limited to, alternate weave patterns, alternate strand dimensions, release coatings (e.g., silicones, fluorochemicals, etc.), static dissipation treatments, and the like. Still other suitable foraminous surfaces that may be employed are described in U.S. Patent Application Publication No. 2007/0049153 to Dunbar, et al.

Regardless of the particular texturing method employed, the tufts formed by the meltblown fibers of the present invention are better able to retain the desired shape and surface contour. Namely, because the meltblown fibers crystallize at a relatively slow rate, they are soft upon deposition onto the forming surface, which allows them to drape over and conform to the contours of the surface. After the fibers crystallize, they are then able to hold the shape and form tufts. The size and shape of the resulting tufts depends upon the type of forming surface used, the types of fibers deposited thereon, the volume of below wire air vacuum used to draw the fibers onto and into the forming surface, and other related factors. For example, the tufts may project from the surface of the material in the range of about 0.25 millimeters to at least about 9 millimeters, and in further embodiments, from about 0.5 millimeters to about 3 millimeters. Generally speaking, the tufts are filled with fibers and thus have desirable resiliency useful for wiping and scrubbing.

Figure 3:
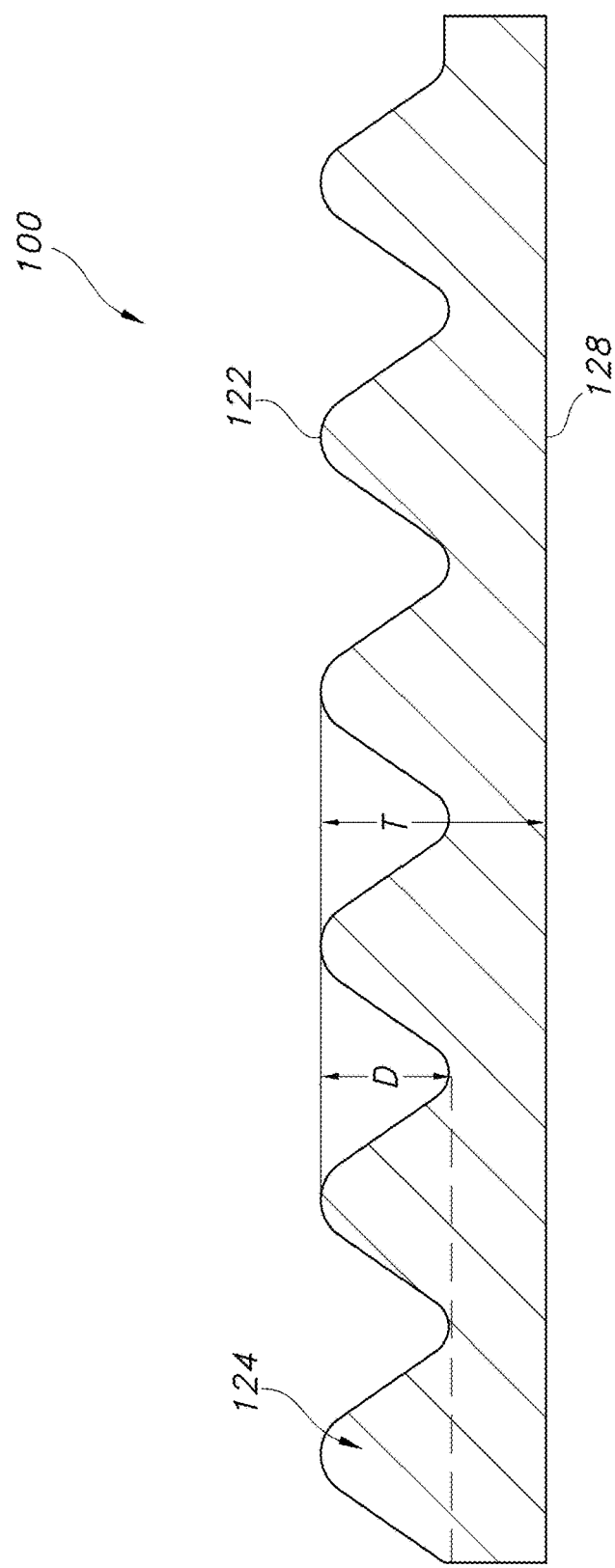
FIG. 3 is a cross-sectional view of one embodiment of a textured coform nonwoven web formed according to the present invention.

FIG. 3 shows an illustration of a cross section of a textured coform web 100 having a first exterior surface 122 and a second exterior surface 128. At least one of the exterior surfaces has a three-dimensional surface texture. In FIG. 3, for instance, the first exterior surface 122 has a three-dimensional surface texture that includes tufts or peaks 124 extending upwardly from the plane of the coform material. One indication of the magnitude of three-dimensionality in the textured exterior surface(s) of the coform web is the peak to valley ratio, which is calculated as the ratio of the overall thickness "T" divided by the valley depth "D." When textured in accordance with the present invention, the coform web typically has a peak to valley ratio of about 5 or less, in further embodiments from about 0.1 to about 4, and in even further embodiments, from about 0.5 to about 3. The number and arrangement of the tufts 24 may vary widely depending on the desired end use. In particular embodiments that are more densely textured, the textured coform web will have from about 2 and about 70 tufts per square centimeter, and in other embodiments, from about 5 and 50 tufts per square centimeter. In certain embodiments that are less densely textured, the textured coform web will have from about 100 to about 20,000 tufts per square meter, and in further embodiments will have from about 200 to about 10,000 tufts per square meter. The textured coform web may also exhibit a three-dimensional texture on the second surface of the web. This will especially be the case for lower basis weight materials, such as those having a basis weight of less than about 70 grams per square meter due to "mirroring", wherein the second surface of the material exhibits peaks offset or between peaks on the first exterior surface of the material. In this case, the valley depth D is measured for both exterior surfaces as above and are then added together to determine an overall material valley depth.

V. Articles

The resilient coform nonwoven web may be used in a wide variety of articles. For example, the web may be incorporated into an "absorbent article" that is capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, mitt wipe, and so forth; medical absorbent articles, such as garments, fenestration materials, underpads, bedpads, bandages, absorbent drapes, and medical wipes; food service wipers; clothing articles; pouches; and so forth. Materials and processes suitable for forming such articles are well known to those skilled in the art. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburder et al., all of which are incorporated herein in their entirety by reference thereto for all purposes. When employed in the absorbent article, the resilient coform of the present invention may form a component of the absorbent core or any other absorbent component of the absorbent article as is well known in the art.

Figure 8:
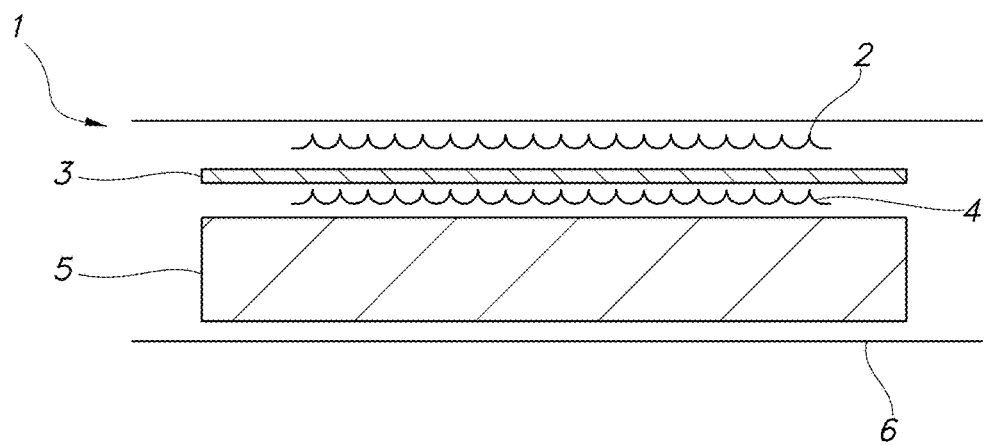
FIG. 8 is a schematic side elevation of a feminine hygiene article.

As one example, the resilient coform nonwoven web may be used as an absorbent member in a feminine hygiene article. As shown in FIG. 8, a feminine hygiene article includes a peel strip 1 which adhesively attaches by means of a garment attachment adhesive 2 to a garment-side barrier film or baffle layer 3 on one side. The other side of the baffle 3 attaches to an absorbent layer 5 with construction adhesive 4. The absorbent layer 5 attaches to a body side liner 6. The resilient coform nonwoven web is suitable used as the absorbent layer 5. Desirably, use of the resilient coform nonwoven web will inhibit bunching of the product as it is worn, hence improving overall effectiveness and reducing leakage. Other suitable configurations for forming personal care articles with absorbent core materials are well known to those skilled in the art. In one desirable embodiment, the resilient coform nonwoven web has a textured surface. The textured surface is desirably positioned towards the body side liner 6 to promote faster fluid intake and higher absorbency of the absorbent core.

In another particular embodiment of the present invention, the coform web is used to form a wipe. The wipe may be formed entirely from the coform web or it may contain other materials, such as films, nonwoven webs (e.g., spunbond webs, meltblown webs, carded web materials, other coform webs, airlaid webs, etc.), paper products, and so forth. In one embodiment, for example, two layers of a textured coform web may be laminated together to form the wipe, such as described in U.S. Patent Application Publication No. 2007/0065643 to Kopacz, which is incorporated herein in its entirety by reference thereto for all purposes. In such embodiments, one or both of the layers may be formed from the coform web of the present invention. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al., which are incorporated herein in their entirety by reference thereto for all purposes. In certain embodiments of the present invention, the wipe is a "wet" or "premoistened" wipe in that it contains a liquid solution for cleaning, disinfecting, sanitizing, etc. The particular liquid solutions are not critical and are described in more detail in U.S. Pat. No. 6,440,437 to Krzysik, et al.; U.S. Pat. No. 6,028,018 to Amundson, et al.; U.S. Pat. No. 5,888,524 to Cole; U.S. Pat. No. 5,667,635 to Win, et al.; and U.S. Pat. No. 5,540,332 to Kopacz, et al., which are incorporated herein in their entirety by reference thereto for all purposes.

The present invention may be better understood with reference to the following examples.

Test Methods

Melt Flow Rate:

The melt flow rate ("MFR") is the weight of a polymer (in grams) forced through an extrusion rheometer orifice (0.0825-inch diameter) when subjected to a load of 2160 grams in 10 minutes at 230° C. Unless otherwise indicated, the melt flow rate was measured in accordance with ASTM Test Method D1238-E.

Thermal Properties:

The melting temperature and crystallization temperature were determined by differential scanning calorimetry (DSC) in accordance with ASTM D-3417. The differential scanning calorimeter was a DSC Q100 Differential Scanning Calorimeter, which was outfitted with a liquid nitrogen cooling accessory and with a UNIVERSAL ANALYSIS 2000 (version 4.6.6) analysis software program, both of which are available from T.A. Instruments Inc. of New Castle, Del. To avoid directly handling the samples, tweezers or other tools were used. The samples were placed into an aluminum pan and weighed to an accuracy of 0.01 milligram on an analytical balance. A lid was crimped over the material sample onto the pan. Typically, the resin pellets were placed directly in the weighing pan, and the fibers were cut to accommodate placement on the weighing pan and covering by the lid.

The differential scanning calorimeter was calibrated using an indium metal standard and a baseline correction was performed, as described in the operating manual for the differential scanning calorimeter. A material sample was placed into the test chamber of the differential scanning calorimeter for testing, and an empty pan is used as a reference. All testing was run with a 55-cubic centimeter per minute nitrogen (industrial grade) purge on the test chamber. For resin pellet samples, the heating and cooling program was a 2-cycle test that began with an equilibration of the chamber to −25° C., followed by a first heating period at a heating rate of 10° C. per minute to a temperature of 200° C., followed by equilibration of the sample at 200° C. for 3 minutes, followed by a first cooling period at a cooling rate of 10° C. per minute to a temperature of −25° C., followed by equilibration of the sample at −25° C. for 3 minutes, and then a second heating period at a heating rate of 10° C. per minute to a temperature of 200° C. All testing was run with a 55-cubic centimeter per minute nitrogen (industrial grade) purge on the test chamber. The results were then evaluated using the UNIVERSAL ANALYSIS 2000 analysis software program, which identified and quantified the melting and crystallization temperatures.

EXAMPLES

Various samples of coform webs were formed from two heated streams of meltblown fibers and a single stream of fiberized pulp fibers as described above and shown in FIG. 1. In various samples, the meltblown fibers were formed from the following polymer compositions:

1. The Example 1 polymer composition was a propylene homopolymer having a density of 0.91 g/cm³, a melt flow rate of 1200 g/10 minute (230° C., 2.16 kg) a crystallization temperature of 113° C., and a melting temperature of 156° C., which is available as Metocene™ MF650X from Basell Polyolefins.
2. The Example 2 polymer composition was a blend of 75 wt % propylene homopolymer (Achieve™ 6936G1) and 25 wt % propylene/ethylene copolymer (Vistamaxx™ 2370, density 0.868 g/cm³, meltflow rate of 200 g/10 minutes (230° C., 2.16 kg)) having a density of 0.89 g/cm³ and a melt flow rate of 540 g/10 minutes (230° C., 2.16 kg), which are available from ExxonMobil Chemical Corp.
3. The Example 3 polymer composition was an olefinic based elastomer (Vistamaxx™2330, density 0.868 g/cm³, meltflow rate of 290 g/10 minutes (230° C., 2.16 kg), ethylene content 13.0 wt %), which is available from ExxonMobil Chemical Corp.

The polymer compositions each further contained 3.0 wt % of surfactant (IRGASURF HL 560, available from Ciba). The pulp fibers were fully treated southern softwood pulp obtained from the Weyerhaeuser Co. of Federal Way, Wash. under the designation "CF-405."

For each Example, the polymer for each meltblown fiber stream was supplied to respective meltblown dies at a rate of 2.0 pounds of polymer per inch of die tip per hour through 0.020 inch diameter holes to achieve a meltblown fiber content of 50 wt %. The distance from the impingement zone to the forming wire (i.e., the forming height) was approximately 12 inches and the distance between the tips of the meltblown dies was approximately 6 inches. The meltblown die positioned upstream from the pulp fiber stream was oriented at an angle of 48° relative to the pulp stream, while the other meltblown die (positioned downstream from the pulp stream) was oriented at an angle of 48° relative to the pulp stream. The forming wire was FORMTECH™ 8 (Albany International Co.). To achieve different types of tufts, rubber mats were disposed on the upper surface of the forming wire. One such mat had a thickness of approximately 0.95 centimeters and contained holes arranged in a hexagonal array. The holes had a diameter of approximately 0.64 centimeters and were spaced apart approximately 0.95 centimeters (center-to-center). Mats of other patterns (e.g., clouds) were also used. A vacuum box was positioned below the forming wire to aid in deposition of the web and was set to 30 inches of water.

Figure 4:
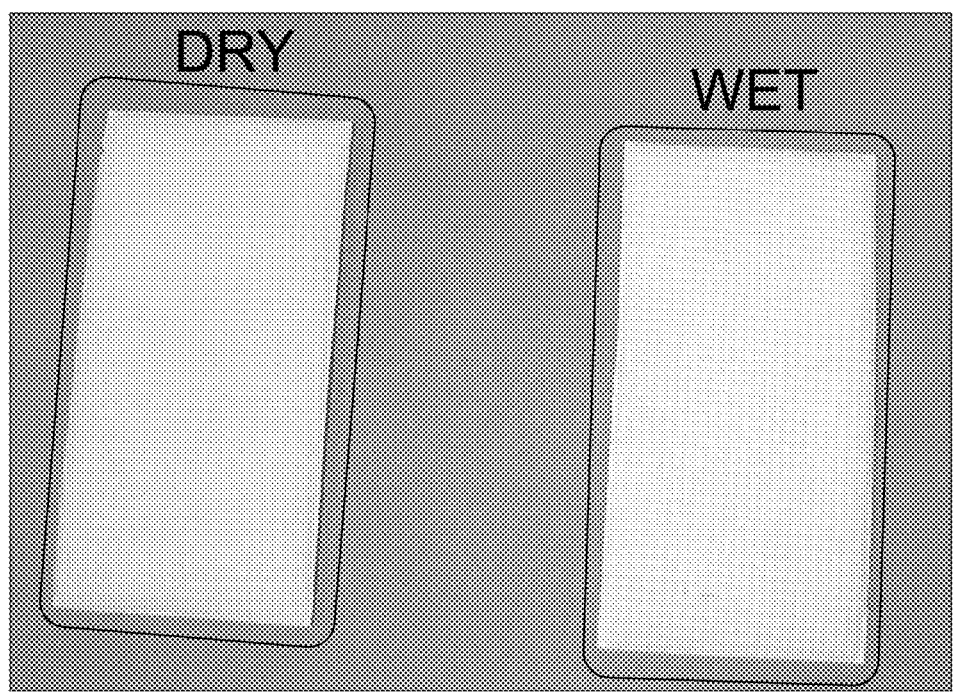
FIG. 4 is a photo of one embodiment of a textured coform nonwoven web.
Figure 5:
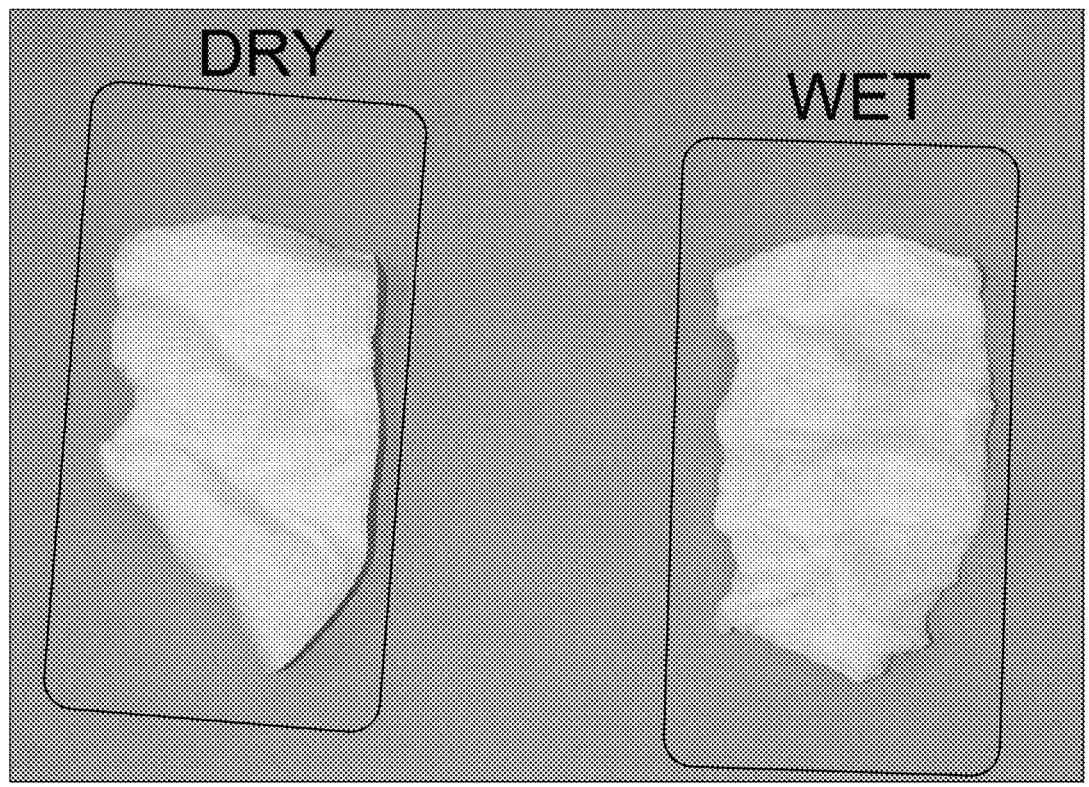
FIG. 5 is a photo of the textured coform nonwoven webs from FIG. 4 after being crumpled and allowed to relax.
Figure 6:
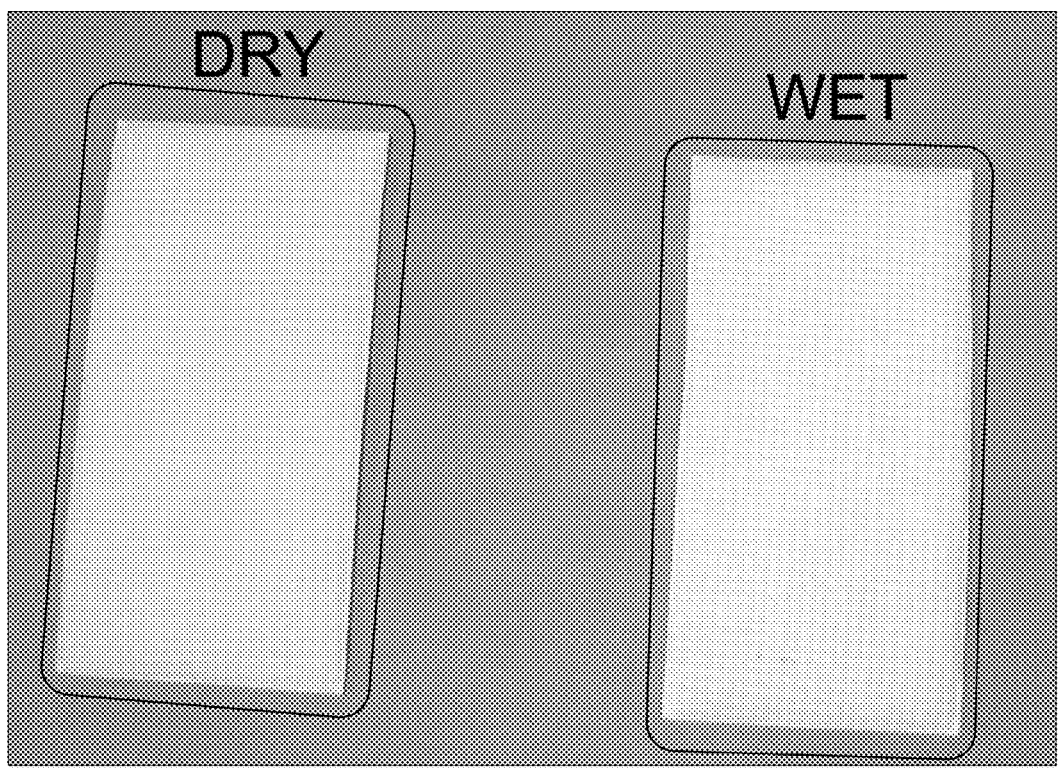
FIG. 6 is a photo of another embodiment of a textured coform nonwoven web.
Figure 7:
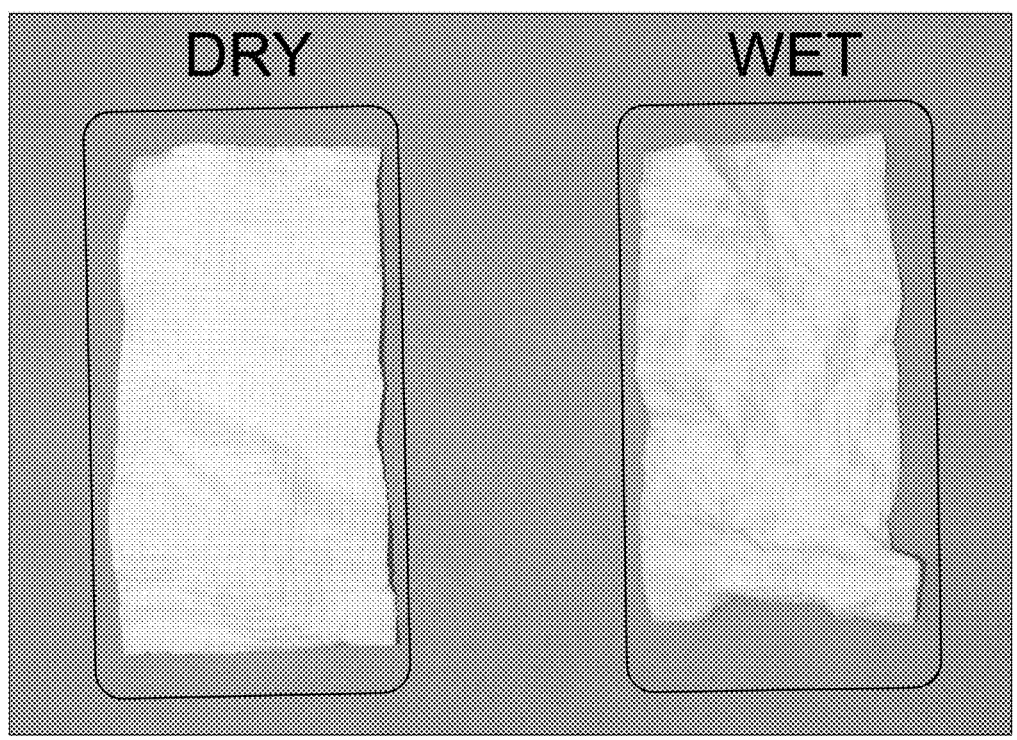
FIG. 7 is a photo of the textured coform nonwoven webs from FIG. 6 after being crumpled and allowed to relax.

To demonstrate the resilient nature of the coform webs, samples of each Example were subjected to a "crumple" test. Each sample was three inches by seven inches. The test was done on both dry and wet samples. The wet samples had 3× its weight in water added to the sample. Each sample was compressed by balling it lightly into a tester's hand where the sample was held for 10 seconds. The samples were then released, lightly shaken out, and laid on a board. The samples were not subsequently smoothed in any way. FIG. 4 shows a photo of Example 1 samples prior to crumpling. FIG. 5 shows a photo of Example 1 samples after completion of the crumple test. FIG. 6 shows a photo of Example 3 samples prior to crumpling. FIG. 7 shows a photo of Example 3 samples after completion of the crumple test. As can be seen in FIGS. 4-7 the Example 3 samples were much more resilient, i.e., opened out much flatter after the crumple test, than Example 1. It was likewise found that the Example 2 samples behaved similar to the Example 3 samples.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto. In addition, it should be noted that any given range presented herein is intended to include any and all lesser included ranges. For example, a range of from 45-90 would also include 50-90; 45-80; 46-89 and the like.

What is claimed is:

1. A method of forming a resilient coform nonwoven web, the method comprising:
    merging together a stream of an absorbent material with a stream of semi-molten meltblown fibers to form a composite stream, wherein the meltblown fibers comprises from 45 wt % to about 99 wt % of the web and the absorbent material comprises from about 1 wt % to about 55 wt % of the web, and further wherein the meltblown fibers are formed from a thermoplastic composition that contains at least one propylene/α-olefin copolymer having a propylene content of from about 60 mole % to about 99.5 mole % and an α-olefin content of from about 0.5 mole % to about 40 mole %, wherein the copolymer further has a density of from about 0.86 to about 0.90 grams per cubic centimeter and the thermoplastic composition has a melt flow rate of from about 120 to about 6000 grams per 10 minutes, determined at 230° C. in accordance with ASTM Test Method D1238-E; and thereafter, collecting the composite stream on a forming surface to form a resilient coform nonwoven web.

2. The method of claim 1, wherein the melt flow rate of the thermoplastic composition is from about 170 to about 1500 grams per 10 minutes.

3. The method of claim 1, wherein the thermoplastic composition comprises from about 0.001 wt % to about 15 wt % of a surfactant.

4. The method of claim 1, wherein the stream of absorbent material is merged together with first and second streams of meltblown fibers.

5. The method of claim 4, wherein the first stream and second stream of meltblown fibers are supplied from respective first and second die heads, each of which is oriented at an angle of from about 45° to 55° relative to a plane tangent to the die heads.

6. The method of claim 1, wherein the web defines an exterior surface having a three-dimensional texture that includes a plurality of peaks and valleys.

7. The method of claim 1, wherein the thermoplastic composition has a crystallization half-time of between about 5 and about 20 minutes.

8. The method of claim 1 wherein the thermoplastic copolymer has a density of from about 0.862 to about 0.88 grams per cubic centimeter.

9. The method of claim 8, wherein the propylene/α-olefin copolymer is single-site catalyzed.

10. The method of claim 1 wherein the propylene/α-olefin copolymer comprises from about 50 to about 99.5 weight % of the thermoplastic composition.

11. The method of claim 10 wherein the thermoplastic copolymer further includes between about 0.5% and about 50 wt. % of a second propylene polymer, and wherein said second propylene polymer is selected from the group consisting of (i) a propylene homopolymer and (ii) a copolymer of propylene and a second comonomer wherein said second comonomer comprises less than about 10% of the second propylene polymer.

12. The method of claim 11, wherein the thermoplastic composition has a crystallization half-time of between about 5 and about 20 minutes.

13. The method of claim 12, wherein the web defines an exterior surface having a three-dimensional texture that includes a plurality of peaks and valleys.

14. The method of claim 13, wherein the thermoplastic composition comprises from about 0.5 weight percent to about 10 weight percent of a surfactant.

15. The method of claim 4, wherein the stream of absorbent fibers is merged together with first and second streams of meltblown fibers whereby the absorbent fibers are incorporated in the coform nonwoven web in a gradient structure such that the absorbent fibers have a higher concentration between outer surfaces of the coform nonwoven web than at the outer surfaces.

16. The method of claim 4 wherein the absorbent fibers are incorporated throughout the web in a substantially homogeneous fashion.

17. The method of claim 1 wherein the α-olefin includes ethylene.

18. The method of claim 1 wherein propylene comprises from 85 mole percent to 98 mole percent of the thermoplastic copolymer and the α-olefin comprises from 2 mole percent to 15 mole percent of the thermoplastic copolymer.

19. The method of claim 1, wherein the absorbent material comprise pulp fibers.

20. The method of claim 19 wherein the absorbent material additionally includes superabsorbent polymer particles or superabsorbent polymer fibers.

* * * * *